United States Patent

Mogensen

[11] Patent Number: 6,149,428
[45] Date of Patent: Nov. 21, 2000

[54] MOULD FOR FORMING A BASIS FOR A DENTAL CAST MODEL

[76] Inventor: Bent Mogensen, 22, Sokkelundsvei, DK-2400 Copenhagen, Denmark

[21] Appl. No.: 09/254,435
[22] PCT Filed: Sep. 10, 1997
[86] PCT No.: PCT/DK97/00382
  § 371 Date: Mar. 9, 1999
  § 102(e) Date: Mar. 9, 1999
[87] PCT Pub. No.: WO98/10709
  PCT Pub. Date: Mar. 19, 1998

[30] Foreign Application Priority Data

Sep. 12, 1996 [DK] Denmark ............... 9600305

[51] Int. Cl.⁷ .................................................. A61C 19/00
[52] U.S. Cl. ............................................. 433/74; 433/34
[58] Field of Search ................................ 433/34, 60, 74

[56] References Cited

U.S. PATENT DOCUMENTS

| | | | |
|---|---|---|---|
| 3,937,773 | 2/1976 | Huffman | 433/74 |
| 4,139,943 | 2/1979 | Dragan | 433/74 |
| 4,449,931 | 5/1984 | Saito | 433/74 |
| 5,328,366 | 7/1994 | Callne | 433/34 |
| 5,466,152 | 11/1995 | Walter | 433/74 |
| 5,658,143 | 8/1997 | Kuperman | 433/64 |

FOREIGN PATENT DOCUMENTS

| | | |
|---|---|---|
| 0629385 | 6/1994 | European Pat. Off. . |
| 3837551 | 5/1990 | Germany . |
| 4218423 | 12/1993 | Germany . |
| 8903662 | 5/1989 | WIPO . |
| 9310719 | 6/1993 | WIPO . |

*Primary Examiner*—John J. Wilson
*Attorney, Agent, or Firm*—Rothwell, Figg, Ernst & Kurz, P.C.

[57] ABSTRACT

A mould for casting a base for a dental model when reconstructing teeth for dentures or parts thereof and including a base plate along the edge of which a mould cavity is placed, the mould cavity including a bottom with fixating structures for the dental model or parts thereof, and walls provided with ribs extending from the bottom, the mould cavity having the shape of at least a part of a jaw. With a view to creating a stable mould, in which the model cast on the base may be remounted and positioned without rocking, the mould is designed in such a way that the fixation structures are at least substantially cylindrical pins which can be inserted in corresponding holes in the bottom of the mould cavity and which each include a portion suited for being cast in the base of the dental model.

4 Claims, 1 Drawing Sheet

MOULD FOR FORMING A BASIS FOR A DENTAL CAST MODEL

BACKGROUND OF THE INVENTION

FIELD OF THE INVENTION

The present invention relates to a mould for casting a base for a dental model when reconstructing teeth for dentures or parts thereof and comprising a base plate, along the edge of which a mould cavity is placed, said mould cavity comprising a bottom with fixating means for the dental model or parts thereof in the form of at least substantially cylindrical pins which can be inserted in corresponding holes in the bottom of the mould cavity and which each comprises a portion suitable for being cast in the base of the dental model, and walls provided with ribs extending from the bottom, the mould cavity having the shape of at least a part of a jaw.

DESCRIPTION OF THE BACKGROUND ART

DE A1 3 837 551 discloses a device for making a dental jaw model divided into segments, the device comprising a carrier plate, on which a socket can be mounted, said socket being provided with guiding grooves which receive separation plates for dividing the model into segments. The carrier plate forming the bottom of the mould cavity constituted by the carrier plate and the socket is provided with preferably conical holes adapted to receive pins or taps, the projecting parts of which are cast in the model.

A mould of a similar type is known from U.S. Pat. No. 5,328,366. When reconstructing teeth in a denture it is usual to cast the model of the denture in a base which is later connected with an articulator, by means of which it is controlled whether the reconstructed teeth are able to correctly engage the corresponding teeth in the opposite jaw. In the known mould it possible to remove the cast model from the mould and mount it again after it has been divided in several pieces, in which connection the tooth to be reconstructed constitutes one of the pieces. When mounting the model in an articulator, the mould is used as a connecting link to the connecting arms of the articulator. When remounting parts of the model in the mould it is important that the individual parts are effectively fixed in the mould. In the known mould it has turned out that the middle part of a model divided in three is not sufficiently fixated, even though it is clamped in a slot extending along the cavity of the mould by means of a fixating means cast into the base part. The middle part can be rocked a few tenths of a millimeter, which means that it is not possible to reconstruct a tooth with optimal accuracy.

SUMMARY OF THE INVENTION

It is, in view of this, the object of the present invention to provide a mould, in which the drawbacks of known moulds have been obviated in practice. This object is met by a mould which is characterized by the novel subject matter of the present.

The invention resides in the realization that even though for the reconstruction of individual teeth in a denture for the jaw model gypsum is used, which has a very little extension during the setting, it is necessary to particularly take this condition in consideration when designing the mould and the fixating means, which are to hold sections of the jaw fixed during the subsequent remodelling. Thus, the profiling of the wall of the mould cannot be expected to be sufficient for securing a jaw section, when, after having been cut away, it is once more mounted in the mould. In the new embodiment the pins are designed as straps which are cast in the jaw model and safely secured, the risk of the model being ruptured being thus eliminated, and each strap comprises two pins, whereby the section is solely fixed in the mould by means of the pins arranged pairwise in this way in the pre-defined position.

A particularly advantageous pattern of placing the holes is created thereby that the sum of the distances in the two rows of holes between adjacent holes is constant in respect of all pairs of holes in the mould, which means that the holes pairwise will acquire the same distance over the whole length of the mould cavity.

In a particularly practical design, the taps are joined into a ribbon by means of a longitudinal rib connecting the middle parts of the bridge. The taps can easily be separated and used as individual straps if desired or inserted as shorter or longer sections in areas, in which the model is later to be divided. If taps and straps are made from plastic, it is unnecessary to take the positioning into account when cutting the jaw model, as the pins may be cut with the same tool as the one used for cutting the model.

When the mould is a full-jaw-mould, it will be advantageous to let the holes go through the bottom of the mould and to let them have the same diameter at both ends. It thus becomes possible to use the under side of the mould for mounting of the model, while it is being handled during the reconstruction of one or more of the teeth. As a consequence of the securing by means of the taps arranged in pairs, the model parts will be stably secured.

To avoid filling holes not used by gypsum during the casting, it is advantageous to provide the holes facing the mould cavity with a film adapted to be penetratable by insertion of a tap. This embodiment facilitates the separation of mould and base part and makes a selective positioning of the pins particularly advantageous.

On account of the stable connection between the mould and model parts remounted therein, it is possible to connect a possible articulator with the mould, if the base plate is provided with means for connection with such a device. A particularly advantageous embodiment is characterized in that the base plate is integral with an articulator comprising a tower made from thermoplastic and provided with a ball-and-socket joint. When adjusting the articulator, the tower is heated to mollify the plastic during the setting of the correct registration between the teeth of the upper denture and the lower denture, the adjustment being performed by bending or pressing the tower in heated and mollified condition to an extent suitable for obtaining the desired registration.

BRIEF DESCRIPTION OF THE DRAWINGS

The invention will be described in detail in the following with reference to the drawing, in which.

DETAILED DESCRIPTION OF THE DRAWING

Figure 1:
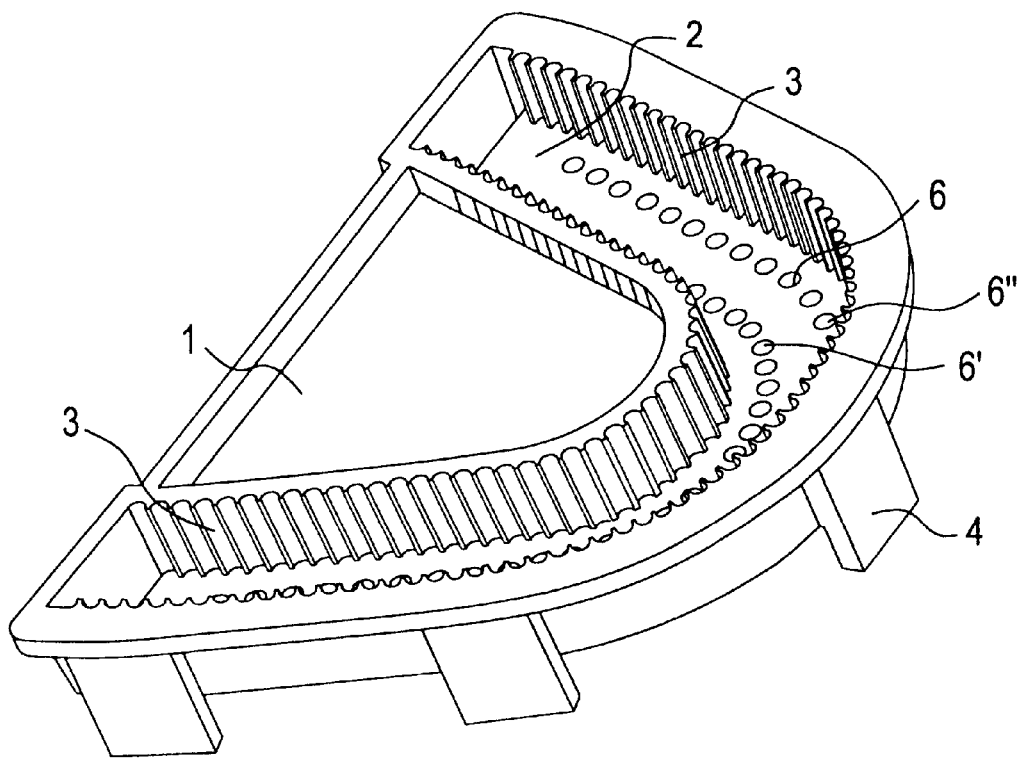
FIG. 1 is an isometric view of a mould according to the invention.

The mould shown in FIG. 1 is adapted for casting a model of a complete jaw in a base part. After casting of a base part, the model with base part is removed from the mould and cut into smaller parts, which are remounted in the mould, while one or more parts of the denture is being reconstructed. The mould shown in FIG. 1 comprises a base plate 1, along the edge of which a mould cavity in the form of a jaw is provided, the mould having a bottom 2 and side walls 3 provided with a rifling or toothing. On the outer side of the side walls 3 supporting legs 4 are provided to lift the under side of the bottom free of the underlayer. In the bottom 2 two rows of holes 6 are provided which consist of pairs of holes 6',6" placed with such regular intervals that if the distance between two adjacent holes in one row is added to the distance between two adjacent holes in the second row, the sum is constant. The holes preferably extend through the bottom and have the same diameter at both ends.

Figure 2:
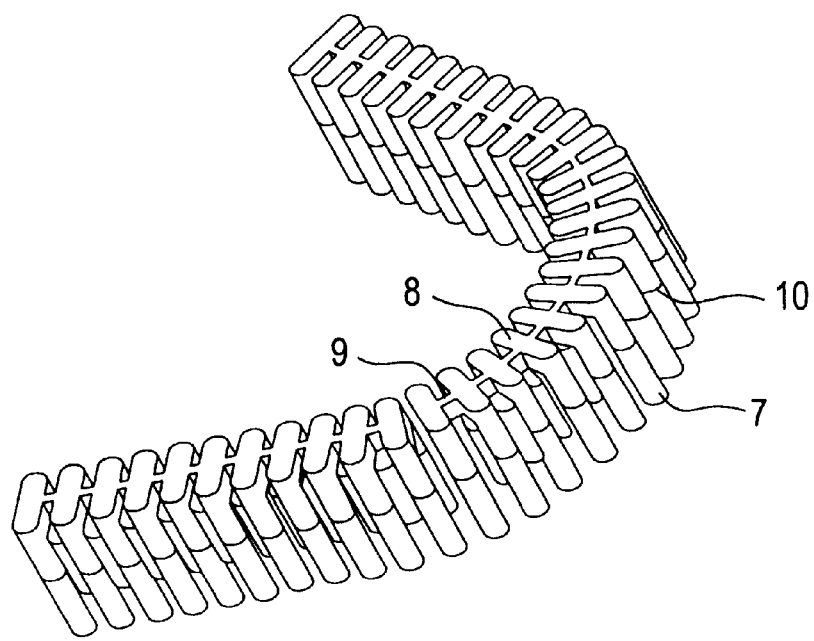
FIG. 2 shows a set of taps in the form of ribbons which are inserted in the mould according to the invention.

Prior to the casting of a base part, taps are inserted in at least a part of the holes, said taps being adapted to be cast in the base part. The taps are connected two by two by means of a bridge, thus constituting a strap. In FIG. 2 straps joined into ribbons and provided with taps 7 are shown, said taps being connected by means of bridges 8, which are in turn connected by means of a longitudinal rib 9. The taps 7 are provided with a collar 10 limiting the depth, with which they may be inserted in the mould. The taps joined into ribbons may be inserted in the mould filling out all holes, or the rib may be broken and the taps inserted as single straps or as short sections. The holes 6 are preferably covered by a thin film of the plastic, from which the mould has been manufactured, the film being so thin that it is easily penetrated by the tap, when it is inserted, but on the other hand so strong, that the gypsum does not flow through the holes when casting the base plate of the model. The mould is for instance manufactured from ABS plastic, if considerable lasting qualities are desired, or for instance styrene plastic, if the aim is a low cost prise, which is advantageous, if the mould is to be discarded after use. The taps may be manufactured from a preferably viscous, hard and smooth plastic, for instance a suitable polyethylene.

The mould may be connected with an articulator, by means of which it may be controlled if the reconstructed teeth can cooperate with the denture of the opposite jaw. In a particular embodiment the mould be manufactured integrally with a tower which with a ball-and-socket joint on top forms one part of the articulator. Correct registration between the two jaw parts are obtained thereby that the plastic in the tower is mollified by heat, which makes it possible to bend or press the tower until a suitable registration is obtained. After cooling, the two jaw parts are moved relative to each other to simulate a chewing movement, partly by means of the ball-and-socket joint, partly by a certain elasticity in the deformed tower.

In the described embodiment of the mould, the mould sides 3 placed opposite one another are rigidly connected with each other by means of the bottom 2, which apart from the holes forms a solid plate. Though the gypsum at the casting extends during the setting by some tenth per cent, the mould sides cannot be pressed apart to an extent, which makes the form sides let go of the cast model. The model will therefore be remountable in the mould and will be secured immovably, also if it has been cut into smaller pieces for reconstruction of individual teeth.

Through the invention features of traditional dental technology are combined with rational use of disposable equipment, which is profitable both in respect of time consumption and to a high extent in respect of accuracy in the work performed.

What is claimed is:

1. A mould for casting a base for a dental model when reconstructing teeth for dentures or parts thereof and comprising a base plate, along the edge of which a bottom with fixating means for the dental model or parts thereof in the form of at least substantially cylindrical pins which are inserted in corresponding holes in the bottom of the mould cavity and which each comprises a portion suitable for being cast in the base of the dental model, and walls provided with ribs extending from the bottom, the mould cavity having the shape of at least a part of a jaw, characterized in that the pins are connected in pairs with a bridge adapted to be cast in the base of the dental model, the holes in the mould cavity bottom being placed in pairs in two rows extending in the longitudinal direction of the bottom, wherein the sum of the distances in the two rows of holes between adjacent holes belonging to two pairs of holes is constant for all the pairs of holes in the mould.

2. A mould according to claim 1, characterized in that the pins are joined to a ribbon by means of a longitudinal rib connecting the middle parts of the bridges.

3. A mould according to claim 1, and in which the mould is a full-jaw-mould, characterized in that the holes are going through the bottom of the mould and have the same diameter at both ends.

4. A mould according to claim 1 in which the mould is a full-jaw-mould, characterized in that the holes are going through the bottom of the mould and have that same diameter at both end.

* * * * *